United States Patent
Van Vaals

(10) Patent No.: US 7,142,700 B2
(45) Date of Patent: Nov. 28, 2006

(54) GEOMETRY MATCHING FOR IMAGING MEDICAL APPARATUS

(75) Inventor: Johannes Jacobus Van Vaals, Eindhoven (NL)

(73) Assignee: Koninklijke Philips Electronics, N.V., Eindhoven (NL)

( * ) Notice: Subject to any disclaimer, the term of this patent is extended or adjusted under 35 U.S.C. 154(b) by 697 days.

(21) Appl. No.: 09/897,364

(22) Filed: Jul. 2, 2001

(65) Prior Publication Data

US 2002/0012457 A1     Jan. 31, 2002

(30) Foreign Application Priority Data

Jul. 10, 2000    (EP) .................................. 00202448

(51) Int. Cl.
    *G06K 9/00*     (2006.01)
(52) U.S. Cl. ....................... 382/128; 382/131; 382/132
(58) Field of Classification Search ........ 382/128–134, 382/151, 209, 282, 284, 294, 278; 600/410, 600/415, 417, 425, 427; 324/307
See application file for complete search history.

(56) References Cited

U.S. PATENT DOCUMENTS

| 5,452,407 A | * | 9/1995 | Crook | 345/421 |
| 5,946,425 A | * | 8/1999 | Bove et al. | 382/294 |
| 6,080,164 A | | 6/2000 | Oshio et al. | 606/130 |
| 6,094,507 A | * | 7/2000 | Monden | 382/195 |
| 6,351,573 B1 | * | 2/2002 | Schneider | 382/294 |

FOREIGN PATENT DOCUMENTS

EP      0946103 A1     9/1999

OTHER PUBLICATIONS

Kall, et al. "Computer-assisted Stereotactic Neurosurgery: Functional Design and Clinical Applications," 1992, IEEE, pp. 1079-1080.*

(Continued)

*Primary Examiner*—Jingge Wu
*Assistant Examiner*—Shefali Patel

(57) ABSTRACT

Anatomical matching of images acquired by different imaging modalities plays an important role in diagnostic medical imaging. In common medical practice such matching takes place after the acquisition of the data sets containing the information to be matched and while utilizing standard post-processing algorithms. The invention provides a method for the acquisition of anatomically matched images while using the information concerning the position and orientation of the first imaging modality relative to the object. Upon selection of a relevant image from the primary data set acquired by means of the first imaging modality, the co-ordinates which unambiguously define the position of the first imaging apparatus relative to this image are defined. These co-ordinates are made available to the second imaging modality which is adjusted in conformity therewith. The image acquired by the second imaging modality will thus be anatomically matched with the primary image.

11 Claims, 2 Drawing Sheets

OTHER PUBLICATIONS

Figure 1:
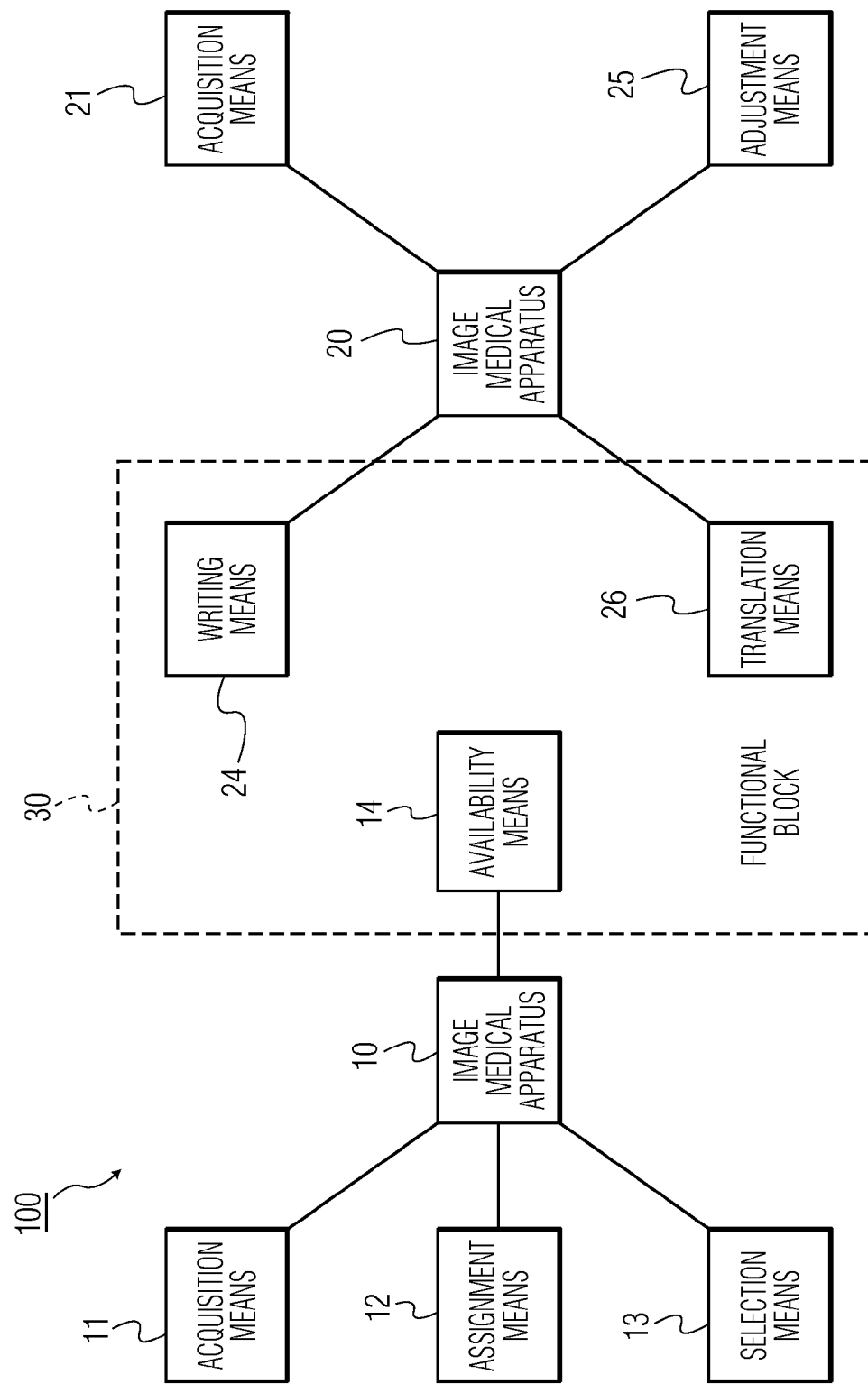

Kall, et al. "Comprehensive Multimodality Surgical Planning and Interactive Neurosurgery," Contempory Issues in Neurological Surgery, Computer in Stereotactic Neurosurgery, Blackwell Scientific Publications, 1992, pp. 209-229.*

Rhode et al., "A System for Real-Time XMR Guided Cardiovascular Intervention," IEEE, Nov. 2005, pp. 1428-1440.*

Gobbi et al., "Integration of Intra-operative 3D Ultrasound with Pre-operative MRI for Neurosurgical Guidance," IEEE, Jul. 23-28, 2000, pp. 1738-1740.*

Article by F.W. Zonneveld "A Decade of Clinical Three-Dimensional Imaging: A Review", Investigative Radiology, vol. 29, No. 7, 1994, pp. 716-725.

Peria O et al., "Using A 3D Position Sensor For Registration Of Spect And Us Images Of The Kidney," Springer Verlag, New York, NY, Apr. 1995, pp. 23-29.

Patent Abstracts Of Japan, Tsujino Hiroyuki, "Diagnostic Device," Publication No. 09024048, Jan. 28, 1997, Application No. 07177456, Jul. 13, 1995.

* cited by examiner

GEOMETRY MATCHING FOR IMAGING MEDICAL APPARATUS

The invention relates to a method of generating anatomically matching images by means of a system which includes at least two imaging medical apparatus.

The invention also relates to a system for carrying out the method.

In contemporary medical practice it is often desirable to examine a patient by means of a plurality of imaging medical apparatus, each imaging medical apparatus producing its own data set for diagnosis or further treatment. The evaluation of cranial disorders is an example of such multifacility diagnosis. It is known that an MR apparatus constitutes a suitable diagnostic facility for the imaging of soft tissues. In the case of, for example, a cranial tumor it may be desirable to image a region of interest of the patient further by means of, for example a CT apparatus and possibly additionally by means of a PET scanner. For the determination of the location of the disorder it is necessary to compare and match the volume data produced by such imaging medical apparatus. In contemporary medical practice all sets of volume data are acquired independently of one another; the matching of the geometries so as to realize anatomically matching images is performed in retrospect by selection and computer reconstruction of the relevant data sets.

Such a method for retrospective matching of the geometries for different images produced by imaging medical apparatus is known from the article by F. W. Zonneveld "A decade of clinical three-dimensional imaging: a review", Investigative Radiology, No. 29, 7, 1994. The cited publication discloses a method for the matching of anatomically corresponding images from data sets already produced by different imaging medical apparatus. The objects to be imaged may be a variety of cranial disorders, for example tumors or neurovascular anomalies. The known method for matching the objects to be imaged utilizes a pattern recognition algorithm in combination with other algorithms, for example, an image reconstruction algorithm. The known matching method has a drawback in that the matching of the relevant objects can take place only in retrospect, so that the matching of the images could be affected by geometrical distortion of the original images. Moreover, such matching methods generally are very time-consuming and their success is highly dependent on the matching algorithm used. Furthermore, execution of such methods necessitates interaction with the user. These problems become critical notably in the case of cranial interventions which must not only be fast but also very precise so as to minimize any side effects of the intervention.

It is an object of the present invention to provide a method of producing anatomically corresponding images by matching the geometries of different imaging medical apparatus in prospective. To this end, the method in accordance with the invention is characterized in that it includes: acquisition of a data set containing a first image by means of a first apparatus; selection of a plane containing the first image from the data set; assignment of first co-ordinates relative to the first apparatus to the plane containing the first image; making the first co-ordinates available to the second apparatus; adjustment of the second apparatus in conformity with the first co-ordinates; formation of the second image while utilizing said adjustment. In conformity with this method an initial acquisition of the data set of a patient is performed by means of the first imaging medical apparatus. In order to relate the spatial position and the orientation of this data set to the spatial adjustment of the first imaging medical apparatus, co-ordinates relative to the first imaging medical apparatus are assigned to said data set. Generally speaking, the data set may be a two-dimensional data set or a three-dimensional data set. A two-dimensional data set is limited to a cross-section of the patient; a three-dimensional data set may contain a number of two-dimensional planes or may consist of intrinsic three-dimensional volume data, that is, no structure of planes is distinguished yet upon storage of this data. Generally speaking, a plane containing information that is relevant to the diagnosis does not correspond to one of the planes of the original two-dimensional data set. A selection step for selecting or reconstructing a plane containing the first image is also required when the data set is a three-dimensional volume data set. This data processing step can be performed by means of reconstruction algorithms that are known per se. After selection of the plane containing the first image, the first coordinates relative to the first imaging medical apparatus are assigned to this plane. The first plane is thus characterized relative to the first imaging medical apparatus. In order to produce an anatomically corresponding image with the second imaging medical apparatus, this apparatus must be adjusted in conformity with the first co-ordinates. This becomes possible by making the first co-ordinates available to the second apparatus. Generally speaking, it is desirable that for the adjustment of the second apparatus in conformity with the first co-ordinates the second apparatus performs a so-called co-ordinate transformation operation so as to calculate own co-ordinates that define a second plane that corresponds to the first plane. A number of imaging medical apparatus could act as the first imaging medical apparatus in the system. In that case the execution of the co-ordinate transformation necessitates the storage of reference co-ordinates for every other imaging medical apparatus in the second imaging medical apparatus. After the second apparatus has been adjusted in conformity with the first co-ordinates, the second image is formed; this second image anatomically corresponds to the first image.

A first version of the method in accordance with the invention is characterized in that the first co-ordinates are made available by means of a computer included in the system. The computer in this version writes in the first co-ordinates of the first imaging medical apparatus. This version offers the advantage that the computer can be arranged in such a manner that the first co-ordinates are made available in a format that suits the second imaging medical apparatus. This may be necessary in a situation where the formats of the first and the second imaging medical apparatus are not compatible. A further advantage of the incorporation of a computer in the system consists in the fact that the computer can be arranged as a central computer in which all information concerning the patients is stored so as to avoid patient identification errors. The presence of a central computer simplifies the data transport between the imaging apparatus in case an essential pause is inserted between the first and subsequent acquisitions of the images. Moreover, the communication protocol of the system may be conceived such that the second imaging medical apparatus itself approaches the central computer concerning the availability of the first co-ordinates.

A further version of the method in accordance with the invention is characterized in that for each connected imaging medical apparatus a reference co-ordinate system is stored in a table present in the computer. This version offers the advantage that all information concerning the reference co-ordinates is stored in the computer so that the individual imaging medical apparatus will not have to follow up on up-to-date information concerning any changes in the configuration of other imaging medical apparatus, for example in a situation where new apparatus have been added or apparatus thus far present have been removed.

A further version of the method in accordance with the invention is characterized in that the second reference co-ordinate system is calculated from the first reference co-ordinate system by the computer. This version offers the advantage that the second imaging medical apparatus does not have to perform the co-ordinate transformation operation, all co-ordinate transformations being performed in the computer.

A further version of the method in accordance with the invention is characterized in that the first co-ordinates are made available via a cable which directly interconnects two imaging medical apparatus. This special version is intended for a situation where a number of imaging medical apparatus, for example two apparatus, co-operate in such a manner that a direct exchange of information is necessary. The use of a cable between these two medical apparatus offers the advantage that the cable for the data transmission is less susceptible to interference than a network or a radio link. An example of such a system with two imaging medical apparatus consists of a combination of an MR apparatus and an X-ray apparatus, both of said apparatus being used, for example to carry out a cardiovascular intervention. During this intervention a patient is immobilized on a patient table that can be transported between these two medical apparatus. Furthermore, a relation is known between the reference co-ordinate systems of these two medical apparatus. After the selection of a first relevant plane within the first data set and after assignment of the first co-ordinates to this first plane, the adjusting co-ordinates are applied to the X-ray apparatus via the data transmission cable. Subsequently, the patient is transported to the X-ray apparatus on the same patient table. The adjusting co-ordinates determine the position of the gantry of the X-ray apparatus relative to the patient table, so that an X-ray image can be formed. The X-ray image of the patient formed in conformity with this method anatomically corresponds to the image of the first plane. This method of co-operation between an MR apparatus and an X-ray apparatus offers the advantage that the exposure projection of the patient by the X-ray apparatus is known a priori. On-line optimization of the exposure projection can thus be dispensed with, so that the overall radiation dose whereto the patient and the staff of the operating room are exposed during such an intervention is reduced.

Figure 2:
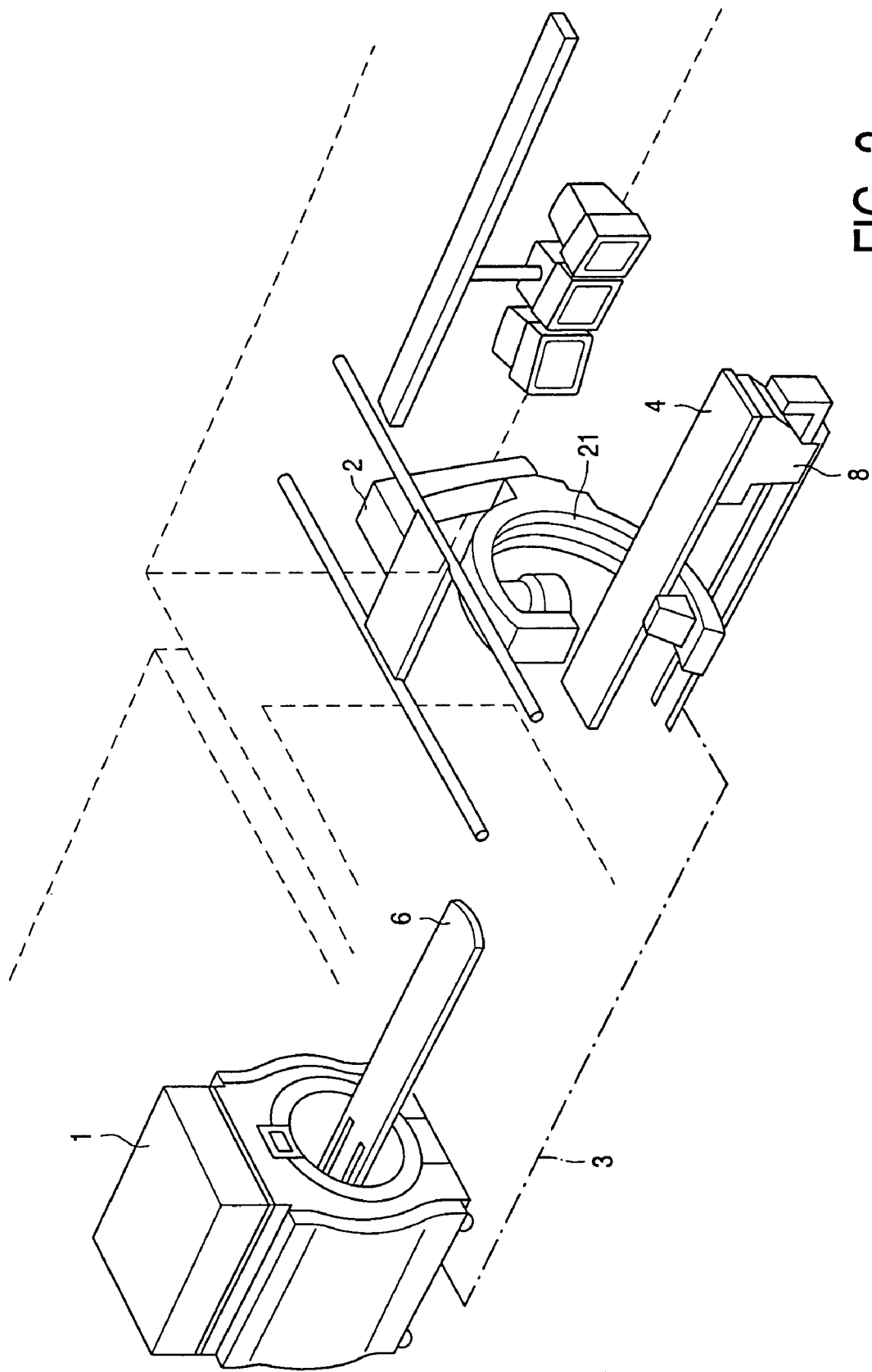

These and other aspects of the invention will be described in detail hereinafter with reference to some Figures; therein:

FIG. 1 illustrates diagrammatically the system for carrying out the method in accordance with the invention, and FIG. 2 shows diagrammatically an example of a system as shown in FIG. 1 in which the apparatus are interconnected by a transmission cable.

FIG. 1 shows diagrammatically an embodiment of a system 100 that is formed by two imaging medical apparatus 10, 20 for carrying out the method for generating anatomically corresponding images in accordance with the invention. The first medical apparatus 100 includes means 11 for the acquisition of the first data set. For example, when the first imaging medical apparatus is an MR apparatus, the device for producing and detecting an RF signal forms part of the means for the acquisition of the first data set. In the case of an X-ray apparatus, the X-ray tube and the X-ray detector form part of the means for the acquisition of the first data set.

For the local assignment of the signal acquired from the studied volume within the patient to the setting of the first apparatus 10, the latter is provided with assignment means 12 which assign the first co-ordinates relative to the first imaging medical apparatus to a plane containing the first image. For cases where a first image that is relevant to the diagnosis is to be selected from the already acquired data set, the first imaging medical apparatus includes selection means 13. An example of such selection means consists of a computer program that executes a data processing step. The assignment means 12 subsequently assign the first co-ordinates to the selected image relative to the first imaging medical apparatus. The first imaging medical apparatus 10 also includes means 14 for making the first co-ordinates available to the second apparatus 20. An example of such means consists of a standard TCP/IP communication protocol. The patient is subsequently examined by means of the second imaging medical apparatus 20 which includes means 21 for the acquisition of an image. In order to adjust the second imaging medial apparatus 20 in conformity with the adjustment of the first imaging medical apparatus relative to the patient, the apparatus 20 includes means 24 for writing in the first co-ordinates made available by the first apparatus 10. This write step can be performed by way of a communication protocol that is known per se, for example by means of a TCP/IP protocol. When the second apparatus is of a type other than the first apparatus, it is necessary to perform a co-ordinate transformation from the first apparatus to the second apparatus. This step can be performed by means of translation means 26. An example of such translation means consists of a conversion table that is stored in the second apparatus. For the acquisition of an image that anatomically corresponds to the first image by means of the second apparatus, the latter must be adjusted in conformity with the first co-ordinates. This step is executed by means of adjusting means 25. Subsequently, the image anatomically corresponding to the first image is acquired by means of the means 21 of the second apparatus 20. If desired, the execution of the operational steps concerning the making available of the first co-ordinates, the writing in of the first coordinates and the translation of the first co-ordinates to the co-ordinates that are suitable for the second apparatus can be delegated to a computer that is included in the system. An example in which said functionalities are delegated to the computer is diagrammatically represented by a functional block 30 in FIG. 1.

FIG. 2 illustrates diagrammatically the co-operation between two imaging medical apparatus 1, 2 for the execution of the method in accordance with the invention, said apparatus being interconnected by means of a data transmission cable 3. The first apparatus 1 is an MR apparatus and the second apparatus 2 is an X-ray apparatus. An example of such co-operation of the two imaging medical apparatus can be found in a suite for cranial interventions in which a region to be treated is defined by means of the MR apparatus and subsequently examined by means of the X-ray apparatus. A patient to be examined is immobilized on a patient table 4 that can be transported between the table support systems 6 and 8 of said apparatus. For a suitable operation of this assembly of medical apparatus it is desirable that the relationship of the respective co-ordinate systems is known and stored, for example, in one of the apparatus. The assembly operates as follows: first an image is formed by means of the MR apparatus 1. Subsequently, a patient is transported, on the same patient table 4, to the X-ray apparatus 2 whereby an anatomically matching image is to be formed. Because of the fact that the position of the patient relative to the patient table is not changed between the exposures by means of the medical apparatus 1 and 2, it is easy to adjust the means 21 for the acquisition of an image anatomically corresponding to the first image by the second apparatus 2. The necessary adjusting parameters are made available to the second apparatus via the data transmission cable 3.

The invention claimed is:

1. A method of generating anatomically matching images from data acquired by at least two interconnected imaging medical apparatus, the method comprising:
   acquiring a data set comprising a first image using a first apparatus;
   selecting a plane within the first image from the data set;
   assigning first co-ordinates to the plane relative to the first image, said first coordinates available by the second apparatus;
   adjusting image data acquired by the second apparatus in conformity with the first co-ordinates, said adjusting further comprising performing a co-ordinate transformation from the first apparatus to the second apparatus; and
   forming a second image based on said adjustment.

2. The method as claimed in claim 1, wherein the first co-ordinates are provided by a computer included in the system.

3. The method as claimed in claim 2, wherein for each of the at least two interconnected imaging medical apparatus, a reference co-ordinate system is stored as a table within the computer.

4. The method as claimed in claim 3, wherein a second reference co-ordinate system is derived based on a first reference co-ordinate system by the computer.

5. The method as claimed in claim 3, wherein a second reference co-ordinate system is calculated from a first reference co-ordinate system by the computer.

6. The method as claimed in claim 1, wherein a data set containing the first image is stored in the computer after acquisition by the first imaging medical apparatus.

7. The method as claimed in claim 1, wherein the first co-ordinates are provided by a cable which directly interconnects each of the at least two imaging medical apparatus.

8. A system for automatically matching medical images generated for different medical imaging apparatus, comprising:
   a first imaging medical apparatus for the acquisition of a first image;
   a second imaging medical apparatus for the acquisition of a second image that anatomically corresponds to the first image;
   means for assigning first co-ordinates relative to the first imaging medical apparatus to a plane defined within the first image, which coordinates are accessible by the second apparatus;
   wherein the second imaging medical apparatus is provided with adjusting means for adjusting a second image reconstructed in conformity with the first co-ordinates such that the second image includes a representation of the plane by a co-ordinate transformation from the first apparatus to the second apparatus.

9. The system as claimed in claim 8, further comprising a computer arranged to provide the first co-ordinates available to the second imaging medical apparatus.

10. The system as claimed in claim 9, wherein the computer is provided with a table, and wherein a reference co-ordinate system is stored for each of the at least two interconnected imaging medical apparatus.

11. The system as claimed in claim 8, wherein the first imaging medical apparatus is an MRI apparatus, and the second imaging medical apparatus is an X-ray apparatus, said apparatus being interconnected by means of a data transmission cable.

* * * * *